US009775631B2

(12) United States Patent
Li et al.

(10) Patent No.: US 9,775,631 B2
(45) Date of Patent: Oct. 3, 2017

(54) GEL SWEEPER FOR RESIDUAL STONE FRAGMENT REMOVAL

(71) Applicant: Boston Scientific Scimed, Inc., Maple Grove, MN (US)

(72) Inventors: Jamie Li, Lexington, MA (US); Timothy P. Harrah, Cambridge, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 234 days.

(21) Appl. No.: 14/208,831

(22) Filed: Mar. 13, 2014

(65) Prior Publication Data

US 2014/0276924 A1  Sep. 18, 2014

Related U.S. Application Data

(60) Provisional application No. 61/788,413, filed on Mar. 15, 2013.

(51) Int. Cl.
*A61B 17/22* (2006.01)
*A61B 17/12* (2006.01)
*A61B 17/00* (2006.01)

(52) U.S. Cl.
CPC .......... *A61B 17/22* (2013.01); *A61B 17/1204* (2013.01); *A61B 17/12031* (2013.01); *A61B 17/12181* (2013.01); *A61B 17/12195* (2013.01); *A61B 2017/00287* (2013.01); *A61B 2017/00951* (2013.01); *A61B 2017/22082* (2013.01)

(58) Field of Classification Search
CPC . A61B 17/0057; A61B 17/0483; A61B 17/22; A61B 17/1204; A61B 17/12031; A61B 17/12181; A61B 17/12195; A61B 17/12036; A61B 17/12186; A61B 17/1219; A61B 17/005; A61B 17/1214; A61B 17/12159; A61B 17/12168; A61B 17/12172; A61B 2017/00623; A61B 2017/0061; A61B 2017/00575; A61B 2017/0496; A61B 2017/22082; A61B 2017/00287; A61B 2017/00951; A61M 29/02; A61M 2029/025
See application file for complete search history.

(56) References Cited

U.S. PATENT DOCUMENTS

| | | | | |
|---|---|---|---|---|
| 3,980,083 A | * | 9/1976 | Elliott | A61J 1/2089 604/203 |
| 4,696,297 A | * | 9/1987 | Pleines | A61B 17/22 606/22 |
| 5,147,318 A | * | 9/1992 | Hohn | A61M 25/0075 604/174 |
| 5,614,204 A | * | 3/1997 | Cochrum | A61B 17/12186 128/DIG. 22 |

(Continued)

*Primary Examiner* — Jocelin Tanner
(74) *Attorney, Agent, or Firm* — Bookoff McAndrews, PLLC

(57) ABSTRACT

Systems and methods for performing medical procedures in body lumens are described. Embodiments of the methods include forming a plug to partially or fully occlude the lumen and moving the plug through a surgical field. Embodiments of the systems include an elongate body graspable by a surgical instrument or by a surgeon that are adapted to anchor to the plug.

18 Claims, 2 Drawing Sheets

(56) References Cited

U.S. PATENT DOCUMENTS

Figure 1:
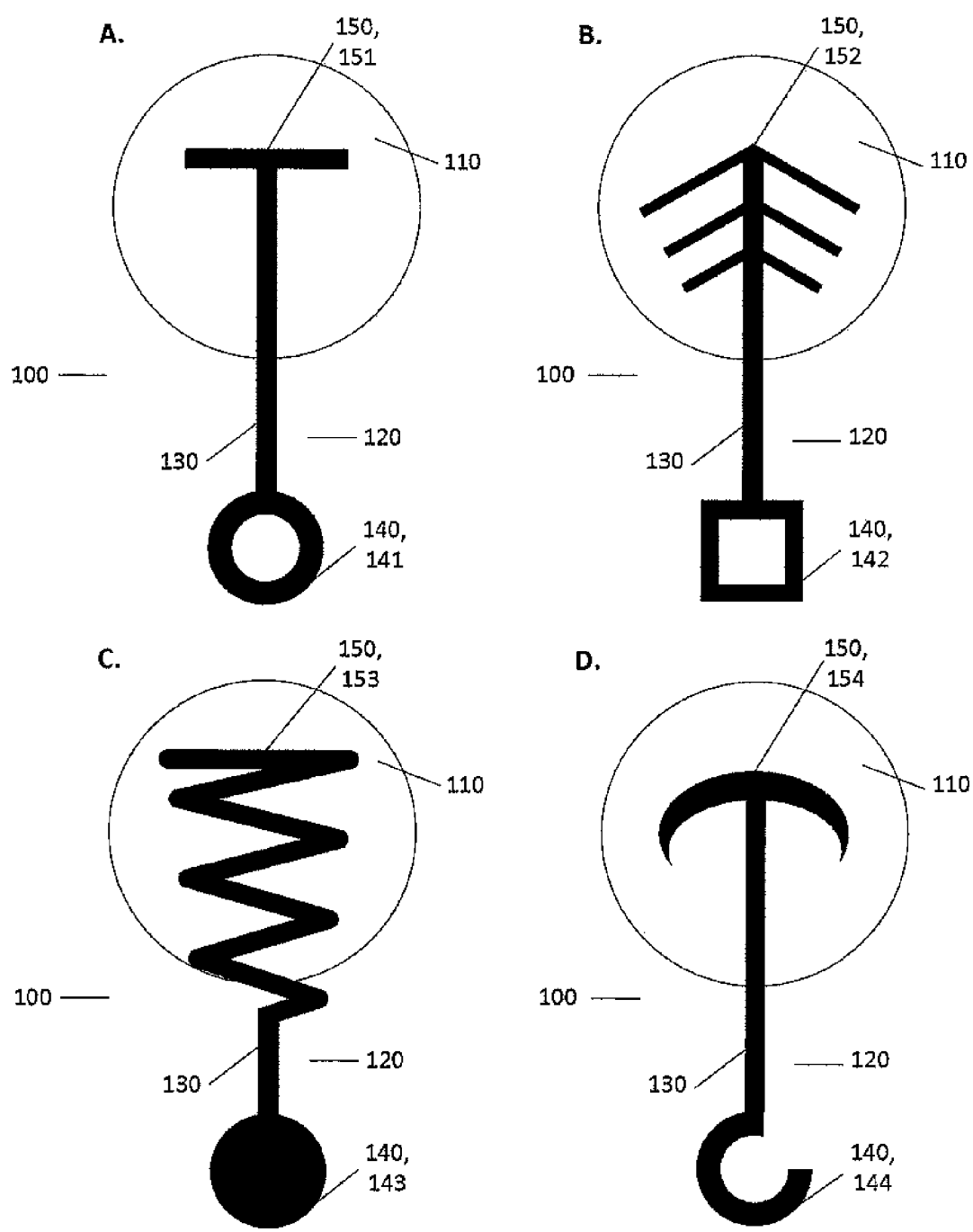

| | | | | |
|---|---|---|---|---|
| 5,749,826 A * | 5/1998 | Faulkner | A61F 2/0009 | |
| | | | 128/DIG. 25 | |
| 5,899,911 A * | 5/1999 | Carter | A61B 17/0469 | |
| | | | 606/139 | |
| 6,360,749 B1 * | 3/2002 | Jayaraman | A61B 17/12172 | |
| | | | 128/898 | |
| 6,368,299 B1 * | 4/2002 | Cimino | A61B 17/22012 | |
| | | | 601/2 | |
| 6,428,513 B1 * | 8/2002 | Abrahamson | A61M 25/0097 | |
| | | | 604/174 | |
| 2001/0044633 A1 * | 11/2001 | Klint | A61B 17/12022 | |
| | | | 606/200 | |
| 2002/0119116 A1 * | 8/2002 | Sahatjian | A61B 17/22012 | |
| | | | 424/78.31 | |
| 2003/0018344 A1 * | 1/2003 | Kaji | A61B 17/12013 | |
| | | | 606/130 | |
| 2003/0018351 A1 * | 1/2003 | Kaji | A61B 17/12022 | |
| | | | 606/191 | |
| 2003/0055440 A1 * | 3/2003 | Jones | A61B 17/12022 | |
| | | | 606/151 | |
| 2004/0158211 A1 * | 8/2004 | Rogers | A61M 25/0097 | |
| | | | 604/284 | |
| 2005/0033314 A1 * | 2/2005 | Sakurai | A61B 17/2202 | |
| | | | 606/127 | |
| 2005/0143678 A1 * | 6/2005 | Schwarz | A61B 17/12022 | |
| | | | 601/4 | |
| 2006/0074409 A1 * | 4/2006 | Schuermann | A61B 17/221 | |
| | | | 606/2.5 | |
| 2006/0206209 A1 * | 9/2006 | Cragg | A61B 17/8811 | |
| | | | 623/17.16 | |
| 2011/0040290 A1 * | 2/2011 | Zadini | A61M 25/0017 | |
| | | | 604/544 | |

* cited by examiner

A.

B.

GEL SWEEPER FOR RESIDUAL STONE FRAGMENT REMOVAL

CROSS-REFERENCE TO RELATED APPLICATION

This application claims priority to 61/788,413 filed Mar. 15, 2013. This application is related to U.S. Pat. No. 7,963,944 issued Jun. 21, 2001, by Sahatjian et al. entitled "Immobilizing Objects in the Body," the entire disclosure of which is hereby incorporated by reference for all purposes.

TECHNICAL FIELD

The invention relates to medical systems and methods for retrieving material from within a body and, more particularly, to methods and systems for removing calculi or concretions such as kidney stones and gallstones from a body lumen of a patient.

BACKGROUND

It is often medically necessary or advisable to remove hard matter, such as kidney stones, gallstones, or foreign bodies from the body of a patient to avoid adverse effects including pain, infection and blockage of body lumens. Removal of hard matter can be done by open surgery, but it is preferable to remove hard matter by minimally-invasive means when possible. Non-invasive removal of hard matter generally involves advancing a specialized device such as a ureteroscope, endoscope, or laparoscope (any or all of which are referred to generally as a "scope") to the location of the hard matter and either retrieving it using a retrieval device such as a stone retrieval basket or pulverizing it by applying energy to the hard matter with, for example, a laser (termed "lithotripsy").

When hard matter is pulverized within a body lumen of a patient, however, the fragments of the hard matter may migrate away from the energy source (termed "retropulsion"). Stone fragments that migrate away from sites of lithotripsy can act as nuclei for the formation of new calculi or concretions and can cause other complications. To minimize the risk of fragment migration, it has become common in lithotripsy procedures to deploy an antiretropulsion device such as the BackStop® polymer system commercialized by Pluromed, Inc. (Woburn, Mass.) and sold by Boston Scientific Corporation (Natick, Mass.). However, the use of antiretropulsion devices inevitably adds time and complexity to lithotripsy procedures. As the average cost of operating room time in the US is $15-$25 per minute, there is an ongoing need to minimize the complexity and time required to deploy and retrieve antiretropulsion devices. (Stahl, J et al., Reorganizing patient care and workflow in the operating room: a cost-effectiveness study, Surgery, 139:717-728, 2006.)

SUMMARY OF THE INVENTION

Embodiments of the current invention reduce the time required for lithotripsy by providing a streamlined mechanism for simultaneously removing polymeric antiretropulsion devices and stone fragments generated during a lithotripsy procedure.

In one aspect, embodiments of the invention provide a sweeper gel system for collecting calculi and preventing retropulsion during a lithotripsy procedure. The system includes, generally, a flowable polymer formulation that is able to form a plug when it is introduced into a body lumen, and an elongated body that has a first end graspable by a medical instrument and a second end adapted to secure the elongated body within the plug. In various embodiments, the plug is tacky, the first end of the elongated body includes a loop or a hook, and the second end can include a plurality of flanges or flukes to secure the elongated body to the plug.

In another aspect, embodiments of the invention provide a method of treating a patient that includes forming a polymer plug in a body lumen of the patient and moving the polymer plug through the body lumen. The method optionally includes contacting the plug with a calculus or concretion within the body lumen. Other embodiments of the invention provide a method of treating a patient that includes flowing a polymer formulation into a body lumen of a patient and forming a tacky plug occluding the lumen, performing a medical procedure in a field next to the plug, and moving the plug through the field to clear debris in the field. In some embodiments, the method may include positioning a resilient elongate body in the path of the flowing polymer formulation so that the elongate body protrudes from the plug, and moving the plug by grasping the elongate body with a medical instrument. The elongate body optionally includes a shank with first and second ends, in which the first end has a ring or enlargement that can be grasped by a medical instrument and the second end includes flanges or flukes that secure the shank to the plug. In various embodiments, the polymer formulation includes a polymer that forms a solid or a highly viscous liquid within the body, which polymer is optionally a poloxamer, alginate, polyethylene glycol, polyvinyl alcohol, or hyaluronic acid.

In yet another aspect, embodiments of the invention provide a kit for performing a medical procedure in a body lumen that includes an elongate body and a polymer formulation capable of forming a plug when flowed into a body lumen.

DRAWINGS

In the drawings, like reference characters refer to like features through the different views. The drawings are not necessarily to scale, with emphasis being placed on illustration of the principles of the invention.

FIG. 1 includes schematic depictions of sweeper gel systems that include mechanical handle means according to certain embodiments of the invention.

Figure 2:
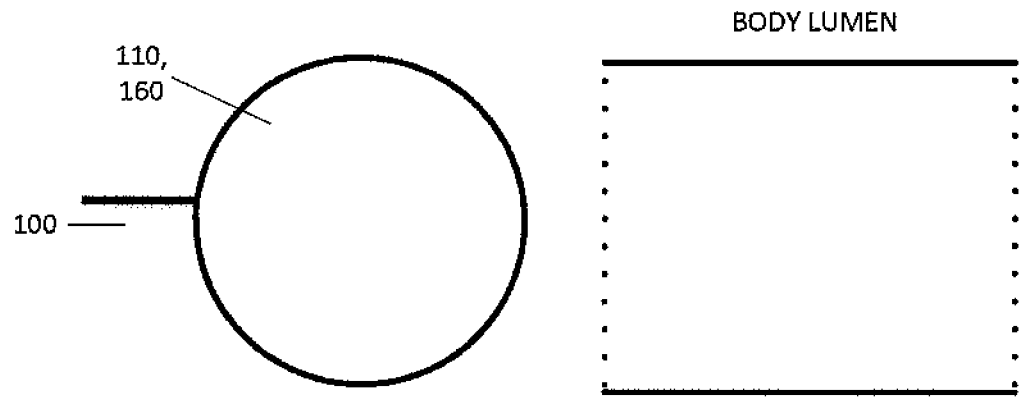
Figure 2:
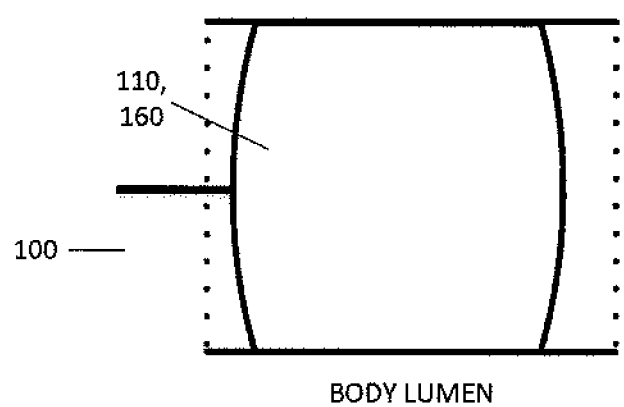

FIG. 2 includes schematic depictions of sweeper gel systems that include a receptacle containing a polymer formulation that forms a gel.

DETAILED DESCRIPTION OF THE PREFERRED EMBODIMENTS

Various exemplary sweeper gel systems 100 for collecting fragmented calculi generated during a medical procedure such as lithotripsy are shown in FIG. 1. The system 100 includes a gel plug 110 formed from a polymer formulation that is initially flowable but, when deposited in a body lumen, hardens to form a plug having a sufficiently high shear modulus to maintain its shape under the forces generated during the procedures described below. Put another way, the plug preferably has sufficient cohesive strength or mechanical integrity to remain intact and keep substantially the same shape when in use. The system 100 also includes a resilient elongate body 120 that acts as a handle that can be anchored into the plug 110. The resilient elongate body 120 generally has first and second ends 140, 150, respectively, and optionally comprises a shank 130 extending for at least part of the distance between the first and second ends 140, 150. The first end 140 of the elongate body 120 includes a portion that is graspable by a medical device, which may be a round loop 141 as shown in FIG. 1A, a non-round loop 142, shown in FIG. 1B, an enlargement or bulbous region 143, as shown in FIG. 1C, or a hook 144 as shown in FIG. 1D. Other suitable structures familiar to those of skill in the art can also be used as means for grasping the elongate body 120, and these structures are within the scope of the invention.

At the second end 150, the elongate body 120 includes means for securing the elongate body 120 to the polymer plug 110. In the exemplary embodiment of FIG. 1A, the second end 150 includes a flange 151 that extends perpendicular to the shank 130 of the elongate body 120 and is shaped to prevent the displacement of the elongate body 120 along the axis defined by the shank 130 when the elongate body 120 is anchored in a plug 110. FIG. 1B shows another exemplary embodiment in which multiple flanges 152 extend at acute angles relative to the second end 150 of the elongate body 120, again to prevent displacement along the axis defined by the shank 130. Other embodiments of the invention utilize a coil 153, as shown in FIG. 1C, or a plurality of curved flukes 154 as shown in FIG. 1D. Any suitable shape can be used for the second end 150 of the elongate body 120 so long as it does not tear the plug 110 or dislodge from it; such shapes are within the scope of the instant invention. In particular, shapes that permit the second end 150 of the elongate body 120 to be inserted into a soft body and/or through a small diameter aperture but which prevent the elongate body 120 from being retracted when tension is applied to the first end 140 are preferred. Thus, preferred shapes for the second end 150 include expandable structures such as umbrellas (FIG. 1D), expanding coils (FIG. 1C) or baskets, and balloons.

The elongate body 120 is, in preferred embodiments, formed from a compliant material selected to minimize the potential for damage body tissues should the elongate body 120 become dislodged from the plug 110 or otherwise impinge upon or impact a body tissue. Suitable materials include, without limitation, silicone, polycaprolactone, polylactic acid, poly(lactic-co-glycolic acid), polyethylene oxide, polypropylene, and other materials known to those of skill in the medical arts. The polymer is preferably biocompatible and optionally bioresorbable. The polymer is optionally, but not necessarily, an elastomer. Additionally, the elongate body 120 can, in some instances, be made of multiple materials, for example having a loop 141 at its first end 140 comprising a loop of suture material and comprising a silicone shank 130 and second end 150. In addition, the elongate body 120 is preferably sufficiently elastic to allow the second end to expand from a relatively compressed, small diameter to a relatively large diameter.

The elongate body 120 preferably has a relatively simple shape, such as those shown in FIG. 1, to simplify its manufacture, as well as its deployment within small diameter body lumens such as ureters.

The plug 110 is formed by flowing a polymer formulation into a body lumen. As used herein, the term "flowing" refers to the introduction of a fluid—a liquid or a gel—through a catheter, while the term "flowable" refers to a fluid or a gel that can be introduced into a body lumen by flowing. Polymer formulations suitable for use in the invention optionally undergo a phase transition during or soon after their introduction into the body: in a first phase, the polymer formulation is characterized by a relatively low viscosity to facilitate flowing the polymer formulation into a body lumen. Once the polymer formulation has entered the body, it preferably transitions into a second phase characterized by a higher viscosity and greater adhesion, which promote the formation of a plug 110 that occludes the lumen and is characterized by a sufficiently high shear modulus or otherwise has sufficient mechanical integrity to remain intact when acted upon by forces applied via the elongate body 120.

Polymer formulations that are configured to undergo a phase transition can comprise one or more low critical solution temperature (LCST) materials, as described in Sahatjian et al. The critical solution temperature—the temperature at which a given material transitions from liquid to gel form—of such LCST materials is advantageously between room temperature (at which LCST materials are liquid) and body temperature (at which LCST materials are gel). Suitable LCST materials include polyoxyethylene-polyoxypropylene (PEO-PPO) block copolymers. Exemplary copolymers of this type include Pluronic acid 1127 and F108, which are PEO-PPO block copolymers with molecular weights of 12,600 and 14,600, respectively (BASF, Mount Olive, N.J.). Other suitable LCST materials include Pluronic acid HOS at concentrations of 20-28% (wt/wt) in phosphate buffered saline (PBS); 22.5% Pluronic acid F108 in PBS; 22% Pluronic acid 1108 in PBS; Pluronic acid F127 at 20-35% PBS; 20% Pluronic acid F127 in PBS. More generally, PEO-PPO block copolymers that are LCST materials and that are biocompatible, biodegradable, and exist as a gel at body temperature and a liquid at below body temperature can also be used to form the plug 110. The molecular weight of a suitable material (such as a block copolymer) can be, for example, between 5,000 and 25,000, and more particularly between 7,000 and 15,000, and, for the two specific compounds identified above, 12,600 or 14,600.

Alternatively, or additionally, the phase-transitioning polymer formulations can include one or more cross-linkable polymers, which can be provided in liquid form and which form gels having a suitably high stress modulus when contacted with cross-linking agents. Suitable cross-linkable polymers include, without limitation, polyacrylic acids, polymethacrylic acid, alginic acid, pectinic acids, sodium alginate, potassium alginate, carboxy methyl cellulose, hyaluronic acid, heparin, carboxymethyl starch, carboxymethyl dextran, heparin sulfate, chondroitin sulfate, polyethylene amine, polysaccharides, chitosan, carboxymethyl chitosan, cationic starch or salts thereof. Suitable cross-linking agents include, without limitation, calcium, magnesium, barium, strontium, boron, beryllium, aluminum, iron, copper, cobalt, lead, silver ions, phosphate, citrate, borate, succinate, maleate, adipate and oxalate ions, and, more broadly, anions or cations derived from polybasic organic or inorganic acids.

The polymer formulations, and the plugs 110 formed therefrom, are preferably water soluble or biodegradable so that any occlusions formed using polymer formulations or plugs 110 according to the invention are temporary rather than permanent. For example, a water soluble plug 110 formed within a ureter can advantageously be removed naturally by the urine. In addition, the polymer formulations balance adhesion and cohesion in a manner that permits a plug 110 of the invention to remain intact when dragged through a body lumen (as described in greater detail below) while passing smoothly and without trauma along the walls of the lumen. The plug 110 formed from the polymer formulation is preferably tacky, so that debris contacting the plug 110 adheres to the plug. Physical characteristics such as tackiness and mechanical strength are affected by the contents of the plug, and may be determined or optimized by changing the plug contents. In particular, the choice of polymer, its molecular weight, and the degree of crosslinking all affect the mechanical properties of the plug, and can all be varied so that the plug can be optimized for a particular application.

In a medical procedure according to an embodiment of the invention, the tip of a scope is inserted into a body lumen of a patient so that the tip is proximate to a site at which a surgical procedure will be performed. A polymer formulation of the invention is then flowed from the tip into the body lumen to form a plug 110 that partially or, more preferably, fully occludes the body lumen, thereby preventing the migration of material through the lumen across the plug. In preferred embodiments, the polymer formulation is flowed around an elongate body 120 so that, when the formulation hardens into a plug 110, the second end 140 of the elongate body 120 protrudes from the plug 110. In other embodiments, however, no elongate body is used.

After the plug is formed, the tip of the catheter or scope is optionally withdrawn and a surgical procedure is performed in a field adjacent to the plug 110. During or after the surgical procedure, a suitable instrument—which may be delivered to the field via the catheter or scope—is used to grasp the plug 110. The grasping can be done directly—i.e. such that the instrument contacts the plug directly or indirectly such that the instrument contacts an elongate member 120 embedded in the plug 110. Once the plug 110 has been grasped, the instrument is used to pull the plug through the lumen toward the catheter or scope. Pulling the plug 110 in this manner results in the plug traveling at least partially through the field, and to the extent that any debris from the surgical procedure (such as fragments of a pulverized hard body, blood clots or dislodged tissue) remains within or near the field, it is preferably swept toward the catheter or scope by the motion of the plug 110. Alternatively or additionally, the scope can be moved toward the plug. In preferred embodiments, the elongate body is deployed, the polymer solution is flowed into the body lumen, and the entire system is retrieved using a single instrument, such as a cystoscope. To facilitate the performance of the different steps, the instrument used in the procedure can include multiple lumens, for example a first lumen dedicated to flowing the polymer formulation and a second lumen that contains a grasping instrument for deploying and/or retrieving the elongate body.

In some embodiments, as discussed above, the plug 110 is tacky, such that as the plug 110 is pulled through the field, debris adheres to the plug 110, thereby minimizing the risk that such debris will migrate away from the field and cause complications. The risk of damage to the walls of the body lumen caused by pulling the plug 110 through the field can be reduced by applying an agent to the plug to reduce friction between the plug 110 and the walls of the body lumen. For instance, a user may flow water over the plug to promote dissolution of the plug and/or its return to the liquid phase. Alternatively, the user may apply a lubricating agent to the plug to form a low friction layer between the plug and a wall of the body lumen.

In an alternate embodiment, shown in FIG. 2, a sweeper gel system 100 also includes a receptacle 160 such as a bag, sponge or balloon that is filled with a polymer formulation 110 as described above. The receptacle, which is preferably sufficiently compliant to be inserted into a tortuous and/or small diameter body lumen is inserted into a body lumen that is to be occluded. As the formulation undergoes the phase transition and forms a gel, as described above, acts to reinforce the receptacle 160, so that the receptacle has sufficient rigidity to occlude the body lumen while withstanding the resulting fluid pressure.

The receptacle 160 can have a closed form (e.g. sponges, bags, balloons) or an open form such that it only partially encloses a gel plug (e.g. umbrella or cup shaped). A suitable open structure preferably covers, encloses or contacts a portion of a solidified gel plug that is sufficient to promote the formation of a relatively compact plug that efficiently occludes a body lumen.

The receptacle 160 may be empty, partially filled, or completely filled with the polymer formulation 110 when it is deployed into the body lumen, and a quantity of polymer formulation 110 is preferably added to the receptacle after the receptacle 160 has been positioned in the body lumen. The receptacle optionally has a lubricious outer surface to permit it to be moved within the body lumen after deployment without risking damage to the walls of the lumen. Additionally, the outer surface of the receptacle can be non-porous and non-permeable to the polymer formulation (e.g. a balloon), or it can be perforated to permit the polymer formulation 110 to flow out of the receptacle and, optionally, directly contact the wall of the body lumen.

The receptacle 160 is graspable by a surgical instrument, and optionally includes protrusions, handles, hooks, baskets, or other features to simplify grasping the receptacle. Systems utilizing receptacles can be used in the same settings, and for the same indications, as systems utilizing elongated members. In fact, in some embodiments, the system includes both a receptacle 160 and an elongated member 120.

While the exemplary methods above focus on the use of a plug 110 and/or an elongate member 120 or a receptacle 160 in conjunction with a (presumably separate) surgical procedure, it should be understood that it is not necessary for a separate surgical procedure be performed, and those of skill in the art will appreciate that a system 100 according to an embodiment of the invention can be used on its own to clear debris or matter, hard or soft, solid or liquid, from any body lumen for any reason. Exemplary applications for the systems and methods of the invention include, without limitation: prevention of retropulsion and gathering of fragmented calculi generated from lithotripsy procedures; removal of concretions or calculi generally; kidney stone removal; gallstone removal; removal of arterial plaques; clearing of the bile ducts; clearance of the pancreatic ducts, removal of foreign matter; and hemostasis. Other applications will occur to those of skill in the art.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A device comprising:
   a polymer formulation having a flowable configuration comprising a gel and a hardened configuration comprising a gel plug including a solid interior; and
   an elongated body having a first end and a second end opposite the first end, the second end including an expandable structure securely embedded within the solid interior of the polymer formulation in the hardened configuration to prevent displacement of the elongated body relative to the gel plug.

2. The device of claim 1, wherein the first end of the elongated body is enlarged relative to a shank of the elongate body.

3. The device of claim 1, wherein the first end of the elongated body includes at least one of a bulbous portion or a hook.

4. The device of claim 1, wherein the elongated body extends along a longitudinal axis, and the expandable structure includes at least one surface extending away from the elongated body in a direction transverse with the longitudinal axis.

5. The device of claim 1, further comprising a receptacle configured to contain at least a portion of the gel plug.

6. The device of claim 1, wherein the gel plug defines an exterior shape in the hardened configuration that remains intact when the gel plug is moved through a lumen by forces applied to the first end of the handle member.

7. The device of claim 6, wherein the exterior shape includes an exterior surface that adheres to debris in the lumen when moved therethrough.

8. A device comprising:
   a hardened gel plug having a solid interior; and
   a handle member having a first end, a second end securely embedded within the solid interior of the hardened gel plug to prevent displacement of the handle member relative to the plug, and a shank extending between the first and second ends,
   wherein the second end of the handle member comprises at least one of a coil, a plurality of curved flukes, or a plurality of flanges extending at an acute angle relative to the shank.

9. The device of claim 8, wherein the first end of the handle member comprises at least one of a bulbous region, a hook, or a loop.

10. The device of claim 8, wherein the at least one of a coil, a plurality of curved flukes, or a plurality of flanges extends perpendicular to the shank.

11. The device of claim 8, wherein the gel plug comprises an exterior shape that remains intact when moved through a lumen by forces applied to the first end of the handle member.

12. The device of claim 11, wherein the gel plug comprises a low critical solution temperature (LCST) material having a critical solution temperature between a room temperature and a body temperature at which the LCST material hardens.

13. The device of claim 8, wherein the at least one of a coil, a plurality of curved flukes, or a plurality of flanges includes an expandable structure.

14. The device of claim 13, wherein the expandable structure is collapsible when the handle member is moved in a first direction and expandable when the handle member is moved in a second direction opposite of the first direction.

15. A device comprising:
   a gel plug formed of a low critical solution temperature (LCST) material having a critical solution temperature between a room temperature and a body temperature at which the LCST material hardens to define a solid interior; and
   a handle member having a first free end, a second end with an expandable structure securely embedded within the solid interior of the gel plug when the LCST material hardens to prevent displacement of the handle member relative to the plug, and a shank extending between the first free end and the second end.

16. The device of claim 15, wherein the expandable structure comprises at least one of a coil, a fluke, or a flange.

17. The device of claim 15, wherein the first free end of the handle member includes an enlargement that is engageable with a medical instrument to move the gel plug through a lumen.

18. The device of claim 15, wherein the LCST material includes one or more cross-linkable polymers.

* * * * *